(12) United States Patent
Eisinger (10) Patent No.: US 11,272,998 B2
(45) Date of Patent: Mar. 15, 2022

(54) STRAIN GAGE FIXATION IN TENSION

(71) Applicant: Covidien LP, Mansfield, MA (US)

(72) Inventor: Joseph Eisinger, Northford, CT (US)

(73) Assignee: Covidien LP, Mansfield, MA (US)

( * ) Notice: Subject to any disclaimer, the term of this patent is extended or adjusted under 35 U.S.C. 154(b) by 136 days.

(21) Appl. No.: 16/809,023

(22) Filed: Mar. 4, 2020

(65) Prior Publication Data

US 2021/0275273 A1 Sep. 9, 2021

(51) Int. Cl.
  *A61B 17/072* (2006.01)
  *A61B 90/00* (2016.01)
  *A61B 17/115* (2006.01)

(52) U.S. Cl.
  CPC .......... *A61B 90/06* (2016.02); *A61B 17/1155* (2013.01); *A61B 2562/0261* (2013.01); *A61B 2562/04* (2013.01)

(58) Field of Classification Search
  CPC ... A61B 90/06; A61B 90/1155; A61B 90/105; A61B 90/072; A61B 90/068
  See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |

(Continued)

FOREIGN PATENT DOCUMENTS

| | | |
|---|---|---|
| CA | 908529 A | 8/1972 |
| CA | 2805365 A1 | 8/2013 |

(Continued)

*Primary Examiner* — Nathaniel C Chukwurah
(74) *Attorney, Agent, or Firm* — Carter, DeLuca & Farrell LLP (57) ABSTRACT

A strain gage assembly for use in a circular stapling device includes a housing having a base portion, an extension portion, and a flange disposed on a free end of the extension portion. A plurality of strain gages is disposed about the extension portion. An anchor supports the housing, and a support is received about the housing and in engagement with the anchor. The strain gages are configured to measure an axial load on the trocar assembly received within the longitudinal passage of the housing. The anchor includes a cylindrical portion having an end and a rim disposed about the end of the cylindrical portion. The anchor defines a cylindrical recess and an opening in communication with the cylindrical recess. The cylindrical recess receives the flange when the extension portion is received within the opening. The support includes a collar for supporting a reload assembly of the circular stapling device.

20 Claims, 7 Drawing Sheets

(56) References Cited

U.S. PATENT DOCUMENTS

| | | |
|---|---|---|
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |

(56) References Cited

U.S. PATENT DOCUMENTS

| | | |
|---|---|---|
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |

(56) References Cited

U.S. PATENT DOCUMENTS

| | | |
|---|---|---|
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 2003/0111507 A1 | 6/2003 | Nunez |
| 2004/0073090 A1 | 4/2004 | Butler et al. |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |

(56) References Cited

U.S. PATENT DOCUMENTS

| | | |
|---|---|---|
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2016/0143641 A1 | 5/2016 | Sapienza et al. |
| 2016/0157856 A1 | 6/2016 | Williams et al. |
| 2016/0174988 A1 | 6/2016 | D'Agostino et al. |
| 2016/0302792 A1 | 10/2016 | Motai |
| 2018/0353186 A1* | 12/2018 | Mozdzierz ............ A61B 17/072 |
| 2018/0360460 A1* | 12/2018 | Mozdzierz ......... A61B 17/3211 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2138118 A2 | 12/2009 |
| EP | 2168510 A1 | 3/2010 |
| EP | 2238926 A2 | 10/2010 |
| EP | 2524656 A2 | 11/2012 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 98/35614 A1 | 8/1998 |
| WO | 0154594 A1 | 8/2001 |
| WO | 2008107918 A1 | 9/2008 |

* cited by examiner

STRAIN GAGE FIXATION IN TENSION

FIELD

This disclosure is generally related to surgical stapling devices and, more particularly, to surgical stapling devices that include an adapter assembly having a strain gage for measuring axial loads during stapling and/or cutting of tissue.

BACKGROUND

Surgical stapling devices include a handle assembly, an elongate body or adapter assembly, including a proximal portion supported on the handle assembly, and a tool assembly supported on a distal portion of the elongate body/adapter assembly. The surgical stapling device may include a strain gage assembly for measuring characteristics of tissue being stapled, e.g., tissue thickness, tissue compression, etc., and/or parameters related to staple formation or tissue cutting, e.g., cutting force, firing force, etc. Typically, a strain gage assembly is supported within the elongate body/adapter assembly.

Surgical stapling devices that utilize strain gages are capable of providing the user with force awareness feedback. Advantages of force awareness feedback include anvil detection, staple detection, cutting to a force for more consistent cutting, controlled tissue compression to avoid tissue damage while maximizing staple formation consistency, excessive load adjustment of stroke to optimize staple formation, and tissue thickness identification.

Due to the sensitivity of a strain gage(s), any unintended forces or strains on the strain gage(s) may negatively impact the accuracy of the device. Strain gages currently in use in circular surgical stapling devices are typically configured to measure bending stresses on the strain gages which are then used to calculate axial stress. These bending stresses can be influenced by small variations in the direction of force on the trocar, and by small variations in the location of the components in the surgical stapling device. Therefore, it would be beneficial to have a mechanism for measuring strain that does not utilize, or is unaffected by, bending stresses on the strain gages.

SUMMARY

A strain gage assembly for use in a circular stapling device is provided. The strain gage assembly includes a housing having a base portion, an extension portion with a free end extending from the base portion and a flange disposed on the free end of the extension portion. The housing defines a longitudinal passage to receive a trocar assembly of the circular stapling device. The assembly further includes a plurality of strain gages disposed about the extension portion of the housing. The plurality of strain gages is configured to measure an axial load on the trocar assembly received within the longitudinal passage of the housing. The assembly also includes an anchor supporting the housing, and a support received about the housing and in engagement with the anchor. The anchor includes a cylindrical portion having an end and a rim disposed about the end of the cylindrical portion. The anchor defines a cylindrical recess and an opening in communication with the cylindrical recess. The cylindrical recess receives the flange of the housing when the extension portion of the housing is received within the opening. The support includes a collar for supporting a reload assembly of the circular stapling device.

In some aspects of the disclosure, the plurality of strain gages includes three strain gages. The housing may define first and second openings in communication with the longitudinal passage of the housing for receiving respective first and second retention pins. The first and second retention pins may be selectively engageable with a trocar housing of the trocar assembly. The support may include a pair of extensions in operable engagement with the rim of the anchor.

In aspects of the disclosure, the flange of the housing includes a rounded outer surface and the opening in the anchor includes a rounded portion corresponding to the rounded outer surface of the flange configured to permit movement of the housing relative to the anchor. The anchor may define first inner and outer slots on a first side of the opening and second inner and outer slots on a second side of the opening, the first and second inner and outer slots being configured to receive inner and outer bands of a drive assembly. The support may be configured to transfer a load from the reload assembly to the housing.

An adapter assembly for connecting a reload assembly to a handle assembly includes a distal portion configured for operable engagement with the reload assembly, a proximal portion configured for operable engagement with a handle assembly, and a strain gage assembly disposed within the distal portion. The strain gage assembly includes a housing, an anchor secured to the housing, and a support disposed about the housing. The housing may define a longitudinal passage. The adapter assembly further includes a trocar assembly received within the housing of the strain gage assembly. The trocar assembly includes a trocar housing and a trocar member slidably disposed within the trocar housing. The strain gage assembly is configured to measure the tensile load experienced by the trocar assembly during a surgical stapling procedure.

In aspects of the disclosure, the housing includes a base portion, an extension portion having a free end extending from the base portion, and a flange disposed on the free end of the extension portion. The strain gage assembly may include a plurality of strain gages disposed about the extension portion of the housing. The plurality of strain gages may be configured to measure an axial load on the trocar assembly when the trocar assembly is received within the longitudinal passage of the housing.

In certain aspects of the disclosure, the anchor includes a cylindrical portion having an end and a rim disposed about the end of the cylindrical portion. The anchor defines a cylindrical recess and an opening in communication with the cylindrical recess. The cylindrical recess receives the flange of the housing when the extension portion of the housing is received within the opening. The support may include a collar for supporting the reload assembly of the circular stapling device.

In some aspects of the disclosure, the plurality of strain gages includes three strain gages. The housing may define first and second openings in communication with the longitudinal passage of the housing for receiving respective first and second retention pins. The trocar assembly may include a trocar housing. The first and second retention pins may be selectively engageable with the trocar housing of the trocar assembly. The support may include a pair of extensions in operable engagement with the rim of the anchor. The flange of the housing may include a rounded outer surface and the opening in the anchor may include a rounded portion corresponding to the rounded outer surface of the flange configured to permit movement of the housing relative to the anchor. The support may be configured to transfer a load from the reload assembly to the housing.

BRIEF DESCRIPTION OF DRAWINGS

Various aspects and features of the disclosure are described with reference to the drawings wherein like numerals designate identical or corresponding elements in each of the several views and.

DETAILED DESCRIPTION

In this description, the term "proximal" is used generally to refer to that portion of the device that is closer to a clinician, while the term "distal" is used generally to refer to that portion of the device that is farther from the clinician. Further, the term "clinician" is used generally to refer to medical personnel including doctors, nurses, and support personnel.

The disclosed devices rely on strain gage assemblies that are configured to effectively eliminate off-axis loading. Eliminating off-axis loading may be accomplished by utilizing strain gage assembly with three or more strain gages configured to compute the force vector magnitude and direction of the off-axis loads and cancelling out these loads, or by utilizing a ball-in-socket configuration to allow for rotational degrees of freedom of the components experiencing the loads.

Figure 1:
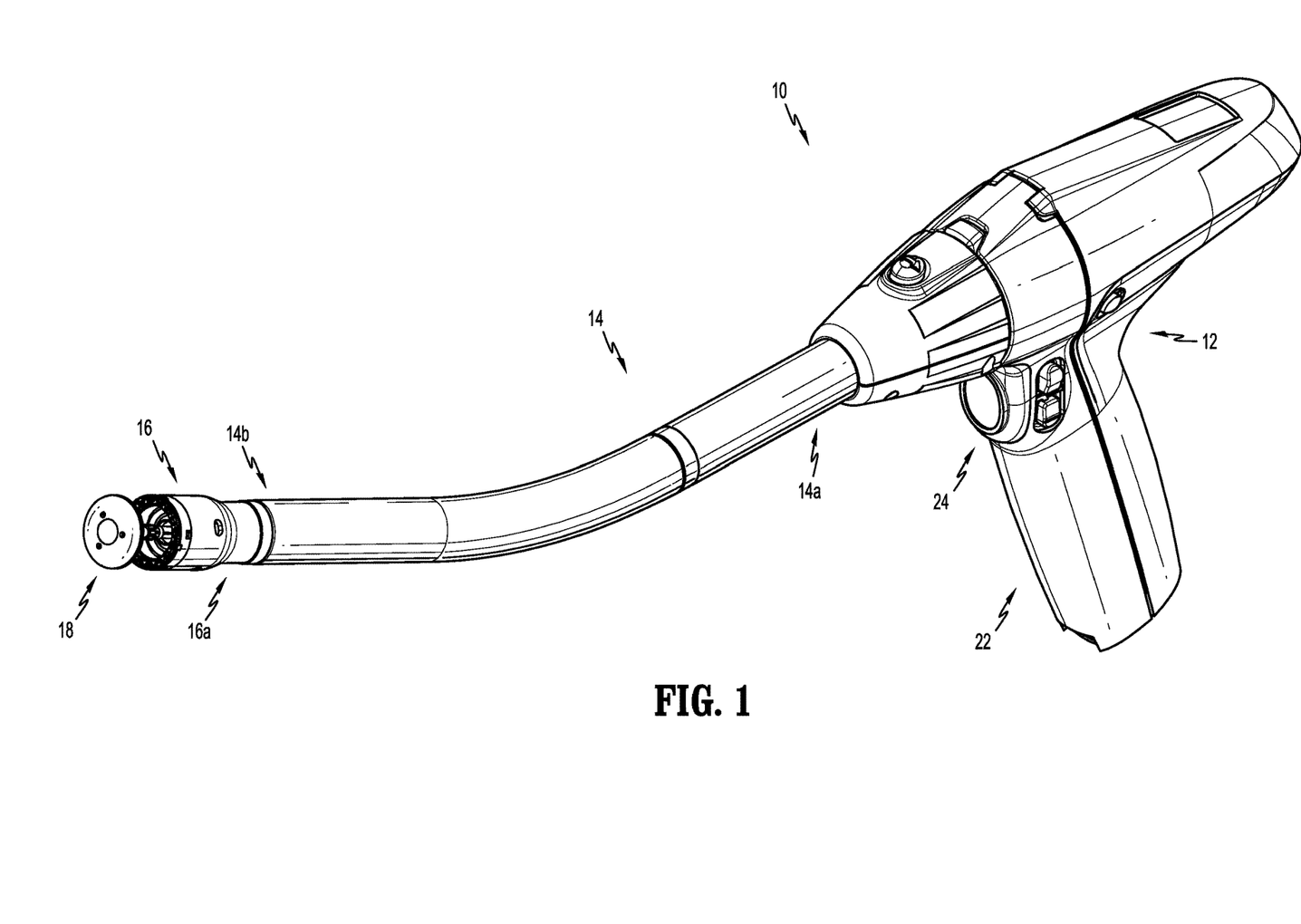
FIG. 1 is a side perspective view of a surgical stapling device including an adapter assembly having a strain gage assembly according to an aspect of the disclosure.

FIG. 1 illustrates a circular stapling device 10 including a handle assembly 12, an elongate body or adaptor assembly 14, a reload assembly 16 releasably supported on the adaptor assembly 14, and an anvil assembly 18 releasably supported for movement in relation to the reload assembly 16 between an open position (FIG. 1) and a clamped position (not shown). The handle assembly 12 includes a stationary grip 22 that supports actuation buttons 24 for controlling operation of various functions of the circular stapling device 10 including approximation of the reload assembly 16 and the anvil assembly 18, firing of staples from the reload assembly 16, and cutting or coring of tissue (not shown). The adapter assembly 14 of the circular stapling device 10 includes a proximal portion 14a that is configured to be releasably coupled to the handle assembly 12 and a distal portion 14b that is configured to be releasably coupled to a proximal portion 16a of the reload assembly 16.

The circular stapling device 10 is illustrated as an electrically powered stapling device including an electrically powered handle assembly 12 that may support one or more batteries (not shown). The adaptor assembly 14 translates power from the handle assembly 12 to the reload assembly 16 and the anvil assembly 18, respectively, to staple and cut tissue. Examples of electrically powered stapling devices can be found in U.S. Pat. Nos. 9,055,943 and 9,023,014, and U.S. Publication Nos. 2018/0125495 and 2017/0340351. Alternately, it is envisioned that aspects of the strain gage assemblies disclosed herein could also be incorporated into stapling devices that are configured for use with robotic systems as disclosed in, e.g., U.S. Pat. No. 9,962,159, that do not include a handle assembly.

Figure 2:
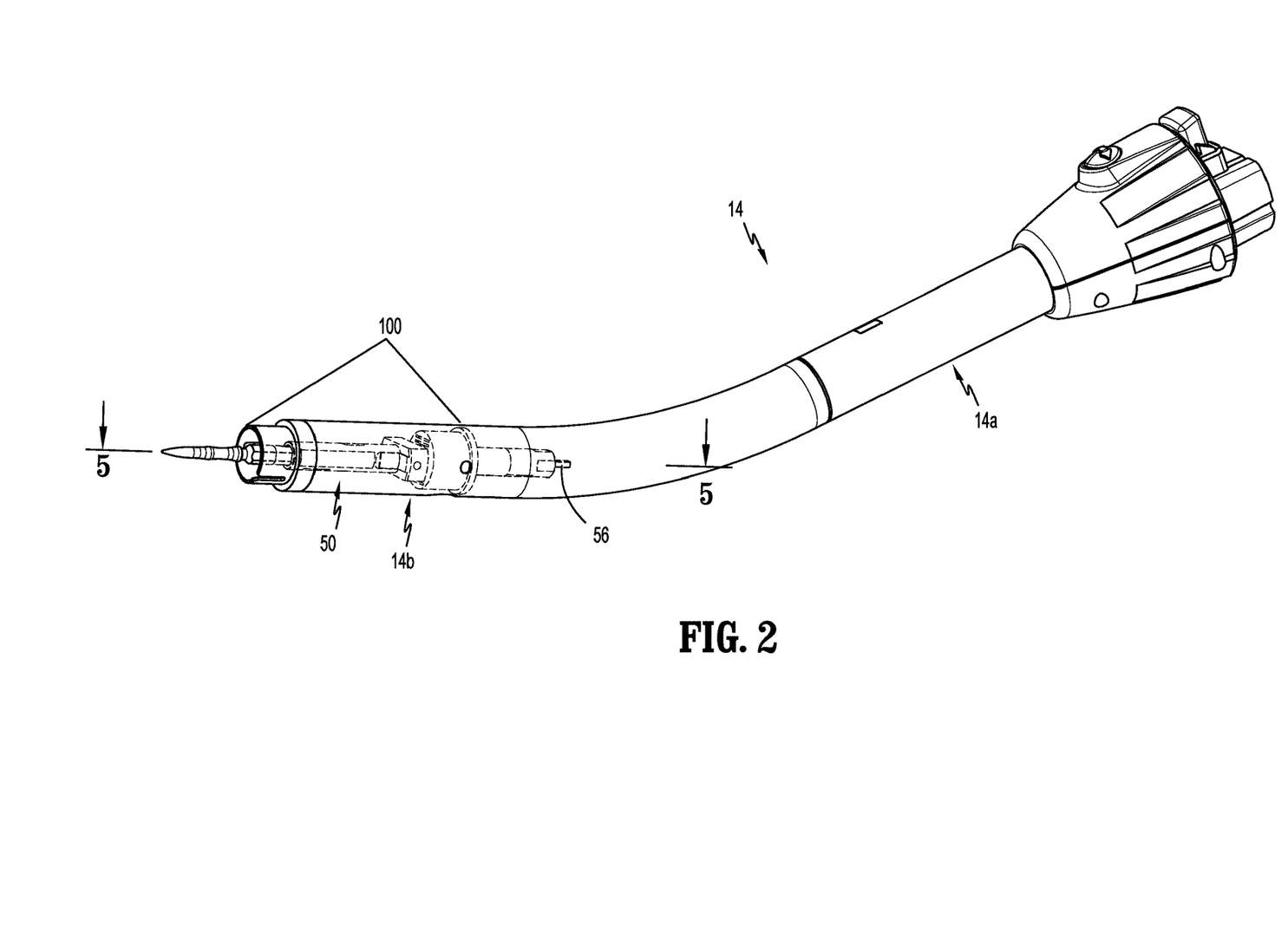
FIG. 2 is a side perspective view of the adapter assembly shown in FIG. 1 with a trocar assembly and strain gage assembly shown phantom.
Figure 3:
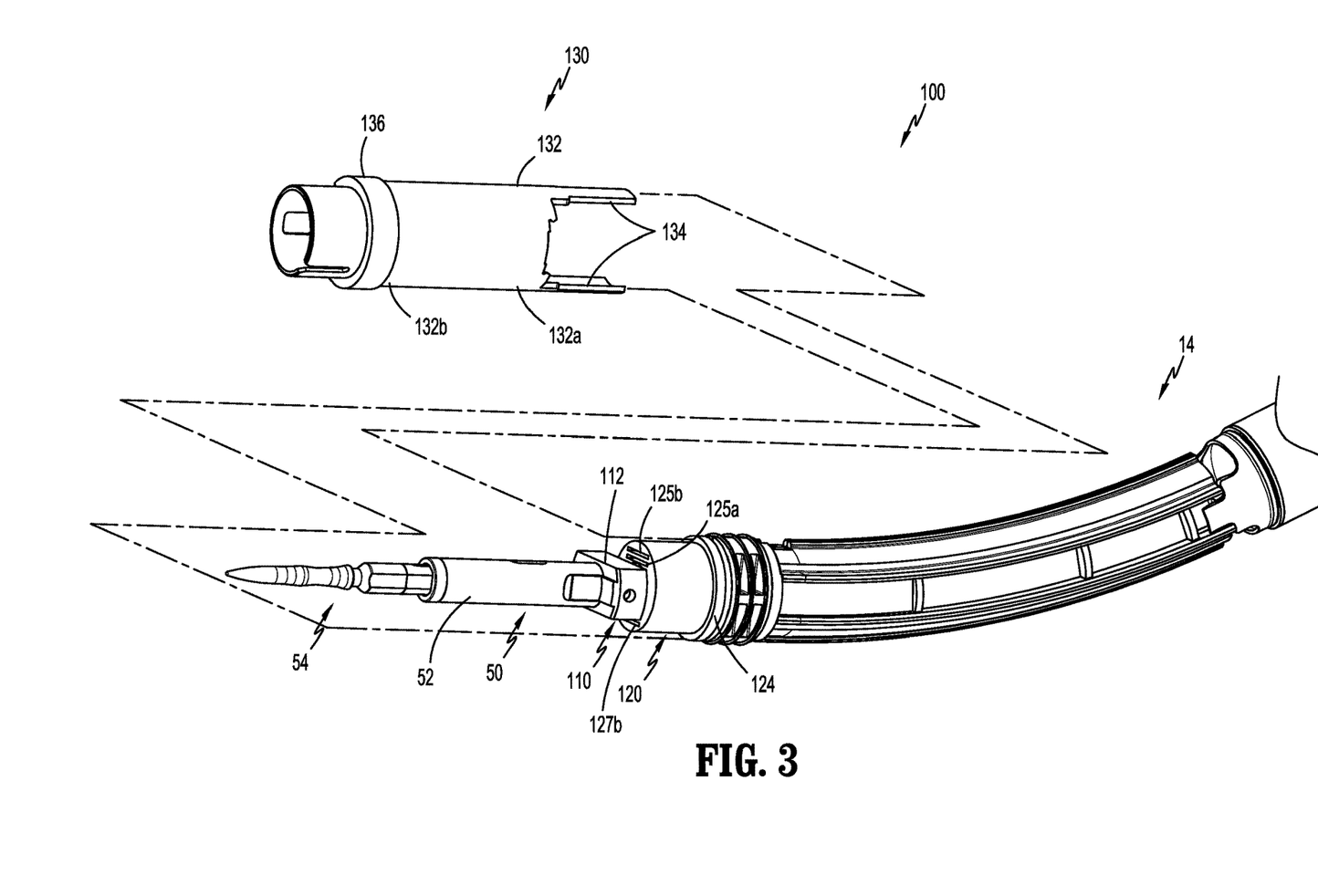
FIG. 3 is a side perspective view of a distal portion of the adapter assembly, with an outer sleeve removed and a tension gage support separated from the adapter assembly.

FIGS. 2 and 3 illustrate a trocar assembly 50 that is releasably received within the distal portion 14a of the adapter assembly 14 of the surgical stapling device 10 (FIG. 1) and is configured to operably engage the anvil assembly 18. The trocar assembly 50 includes a trocar housing 52 (FIG. 3), a trocar member 54 slidably disposed relative to the trocar housing 52, and a drive member or screw 56 (FIG. 2) for advancing and retracting the trocar member 54 relative to the trocar housing 52. The trocar housing 52 defines a pair of openings 53 configured to facilitate attachment of the trocar assembly 50 within the adapter assembly 14.

Figure 4:
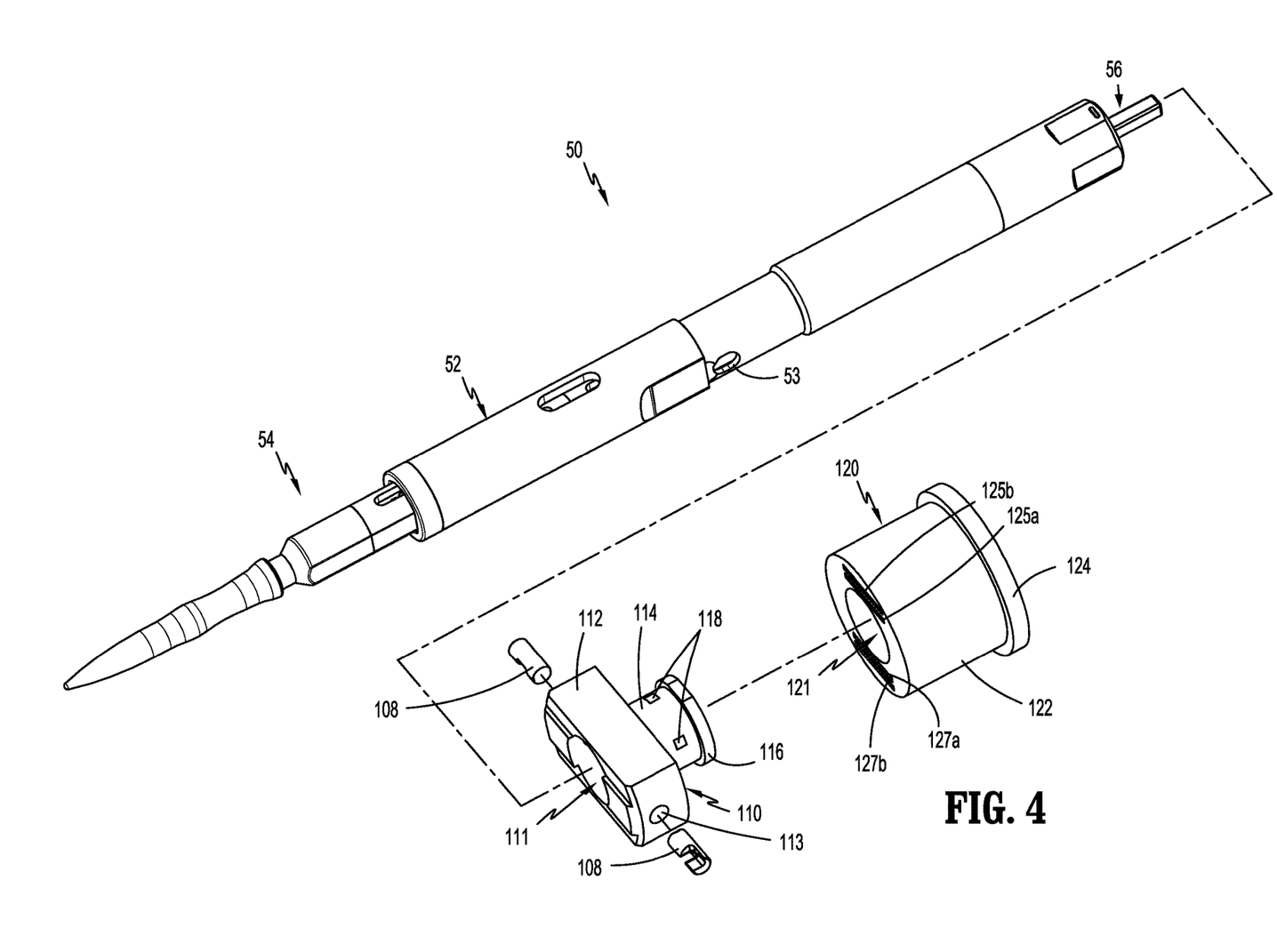
FIG. 4 is a side perspective view of the trocar assembly and a tension gage housing and tension gage anchor of the strain gage assembly shown in FIG. 2.

FIGS. 2-4 illustrate a mechanism for measuring uniaxial strain experienced by the trocar assembly 50 during operation of the circular stapling device 10 (FIG. 1) according to an aspect of the disclosure, shown generally as strain gage assembly 100. The strain gage assembly 100 is disposed within the distal portion 14a of the adapter assembly 14 of the circular stapling device 10 and includes a tension gage housing 110, a tension gage anchor 120 in operable engagement with the tension gage housing 110 for anchoring the tension gage housing 110, and a tension gage support 130 (FIG. 3) in operable engagement with the tension gage anchor 120 for transferring loads from the reload assembly 16 to the tension gage housing 110.

The tension gage housing 110 of the strain gage assembly 100 includes a base portion 112 and an extension portion 114 extending from the base portion 112. A flange 116 is formed on a free end of the of the extension portion 114. The base portion 112 and extension portion 114 of the tension gage housing 110 define a longitudinal passage 111 that receives the trocar assembly 50. The base portion 112 of the tension gage housing 110 defines a pair of openings 113 in communication with the longitudinal passage 111. The openings 113 receive retention pins 108. The retention pins 108 releasably engage the trocar housing 52 of the trocar assembly 50 when the trocar assembly 52 is supported within the adapter assembly 14. More particularly, the openings 113 align with the openings 53 in the trocar housing 52 of the trocar assembly 50 when the trocar assembly 50 is received within the adapter assembly 14 and the retention pins 108 are releasably received within the openings 53 in the trocar housing 52

Strain gages 118 are mounted on the extension portion 114 of the tension gage housing 110 of the strain gage assembly 100. Although shown including three strain gages 118, it is envisioned that the strain gage assembly 100 may have more than three strain gages 118. The strain gages 118 are mounted on the extension portion 114 of the tension gage housing 110 in a manner that directly measures uniaxial tensile stress experienced by the strain gage assembly 100. More particularly, the strain gages 118 are oriented to measure the uniaxial tensile stress experienced by the trocar assembly 50 which is secured to the tension gage housing 110 of the strain gage assembly 100 by the retention pins 108. Known techniques of calculating tensile stress rely on one or more strain gages placed on a plane transverse to the load axis that measure the load experienced in the trocar assembly 50 as a bending stress that is then converted by a processor (not shown) within the handle assembly 12 (FIG. 1) into to a tensile force measurement. By directly measuring the uniaxial tensile stress experienced by the trocar assembly 50 and by computing the force vector direction and magnitude of the load within the adapter assembly 14, the effect of off-axis loading of the trocar assembly 50 and/or component location shifts of the circular stapling device 10 (FIG. 1) are effectively eliminated.

The tension gage anchor 120 of the strain gage assembly 100 includes a cylindrical body portion 122 having a rim 124 formed on a proximal end of the cylindrical body portion 122. The rim 124 of the tension gage anchor 120 is engaged by the tension gage support 130 and transfers a load from the reload assembly 16 to the tension gage housing 110. The tension gage anchor 120 defines a cylindrical recess 121 having a first diameter, and an opening 123 in communication with the cylindrical recess 121 having a second diameter. The first diameter is larger than the second diameter. The cylindrical recess 121 of the tension gage anchor 120 receives the flange 116 of the tension gage housing 110 when the extension portion 114 of the tension gage housing 110 is received within the opening 123 in the tension gage anchor 120.

The cylindrical body portion 122 of the tension gage anchor 120 further defines inner and outer slots 125a, 125b on a first side of the opening 123 and inner and outer slots 127a, 127b of a second side of the opening 123. The inner slots 125a, 127a receive first and second inner bands 140a, 140b (FIG. 8) of a drive assembly (not shown) and the outer slots 125b, 127b receive first and second outer bands 142a, 142 of the drive assembly. The first and second inner bands 140a, 140b are configured to advance a circular knife assembly (not shown) that is supported within the circular reload 16 (FIG. 1) and the first and second outer bands 142a, 142b are configured to advance a staple pusher assembly (not shown) supported within the circular reload 16.

Figure 5:
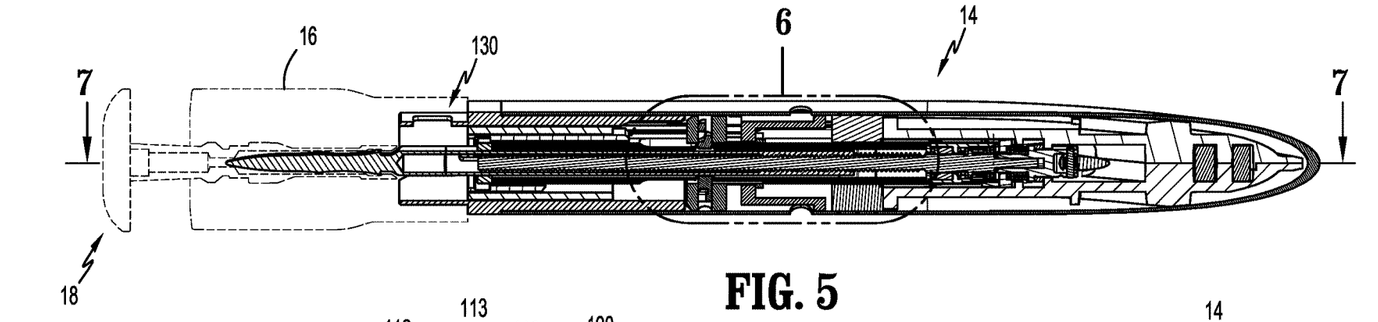
FIG. 5 is a cross-sectional view taken along section line 5-5 shown in FIG. 2.
Figure 6:
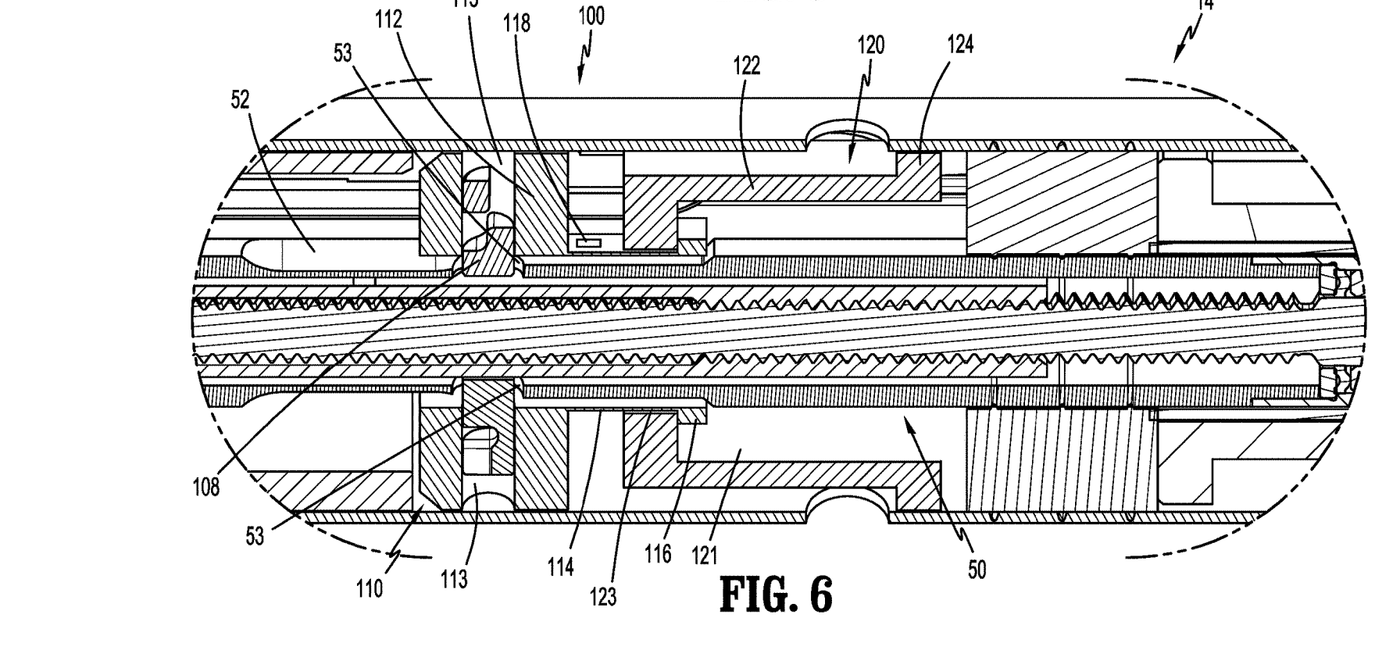
FIG. 6 is an enlarged view of the indicated area of detail shown in FIG. 5.

FIGS. 5 and 6 illustrate the flange 116 (FIG. 6) of the tension gage housing 110 of the strain gage assembly 100 securing the tension gage housing 110 to the tension gage anchor 120. More particularly, when the extension portion 114 of the tension gage housing 110 is received through the opening 123 in the tension gage anchor 120, the flange 116 of the tension gage housing 110 engages the tension gage anchor 120 to secure the tension gage housing 110 relative to the tension gage anchor 120.

Figure 7:
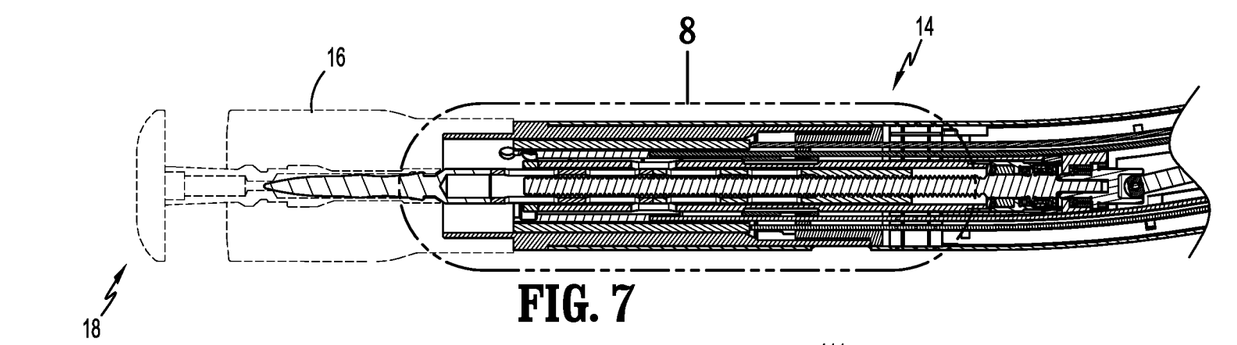
FIG. 7 is a cross-sectional view taken along section line 7-7 shown in FIG. 5.
Figure 8:
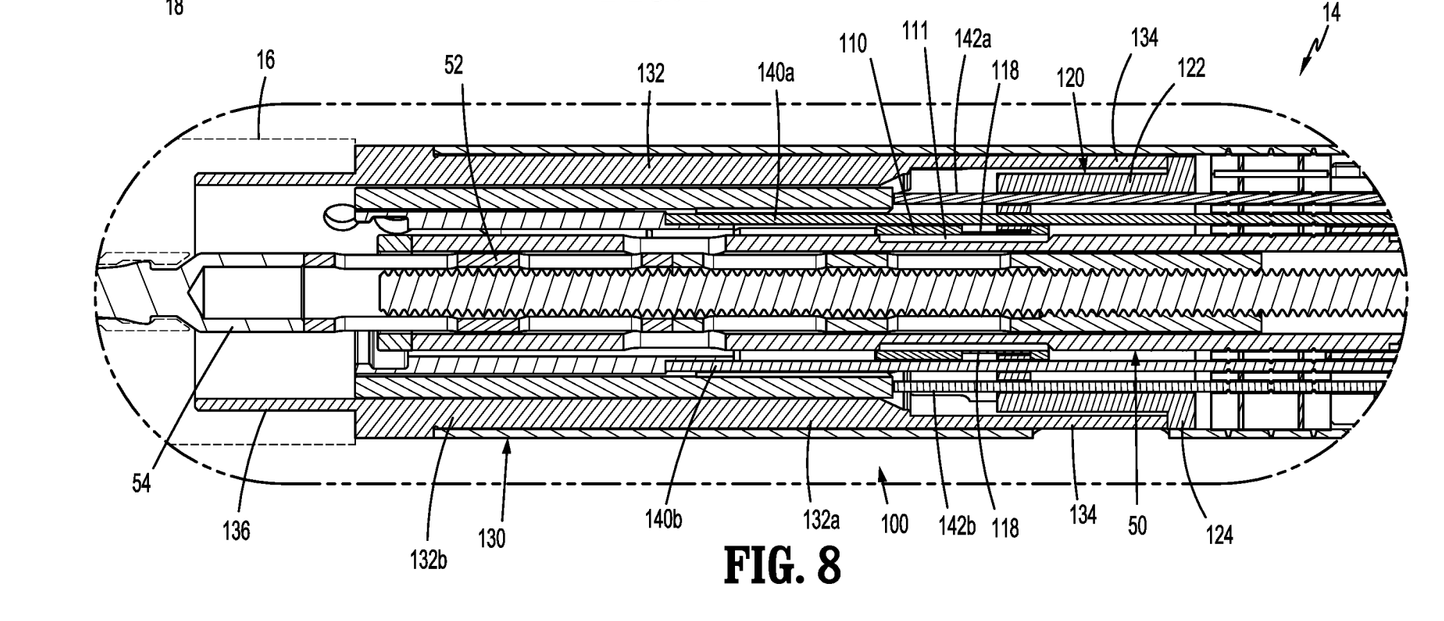
FIG. 8 is an enlarged view of the indicated area of detail shown in FIG. 7.

FIGS. 7 and 8 illustrate the tension gage support 130 of the tension gage assembly 100 includes a cylindrical body 132 having a pair of extensions 134 on a proximal end 132a and a collar 136 on a distal end 132b. Although shown having two extensions 134, it is envisioned that the tension gage support 130 may have more than two extensions. The extensions 134 engage the rim 124 of the tension gage anchor 120 and transfer the load experienced in the reload assembly 16 (FIG. 1) during a stapling procedure to the tension gage anchor 120. The collar 136 of the tension gage support 130 releasably engages the reload assembly 16.

The trocar assembly 50 is supported within the adapter assembly 14 and is in operable engagement with the strain gage assembly 100. More particularly, the trocar assembly 50 is received through the longitudinal passage 111 in the tension gage housing 110 of the strain gage assembly 100 and the retention pins 108 (FIG. 8) secure the trocar housing 52 of the trocar assembly 50 relative to the tension gage housing 110. The anvil assembly 18 is secured to the trocar member 54 of the trocar assembly 50 and the reload assembly 16 is secured to the collar 136 of the tension gage support 130. The tension gage support 130 includes extensions 134 which engage the tension gage anchor 120 and transfer the load experienced by the reload assembly 16 to the tension gage anchor 120.

During operation of the circular stapling device 10 (FIG. 1), the anvil assembly 18 is approximated relative to the circular reload assembly 16 to clamp and staple tissue (not shown). Any axial loading experienced within the trocar assembly 50 through interaction of the anvil assembly 18 with the reload assembly 16 is measured directly by the strain gages 118 supported on the extension portion 114 of the tension gage housing 110. Similarly, any axial or off-axial loading experienced within the reload assembly 16 through interaction of the anvil assembly 18 with the reload assembly 16 is transferred to the tension gage housing 110 through the tension gage support 130 and the tension gage anchor 120.

The strain gage assembly 100 provides data to a processor (not shown) in the handle assembly 12. The processor in the handle assembly 12 includes an algorithm configured to compute the force vector direction and magnitude of the loading forces experienced within the adapter assembly 14 and effectively eliminate the effect of off-axis loading of the trocar assembly 50.

Figure 9:
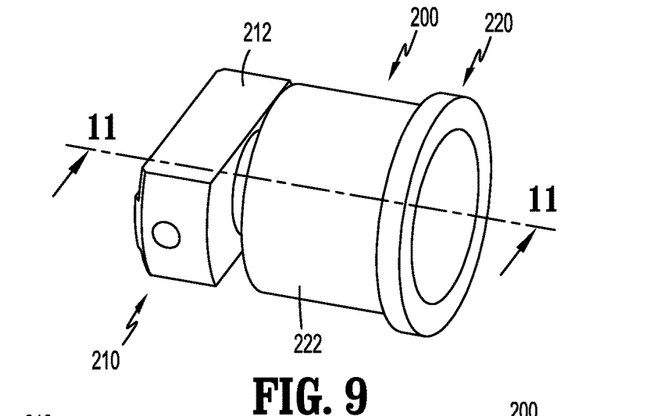
FIG. 9 is a perspective view of a tension gage housing and a tension gage anchor of a strain gage assembly according to another aspect of the disclosure.
Figure 10:
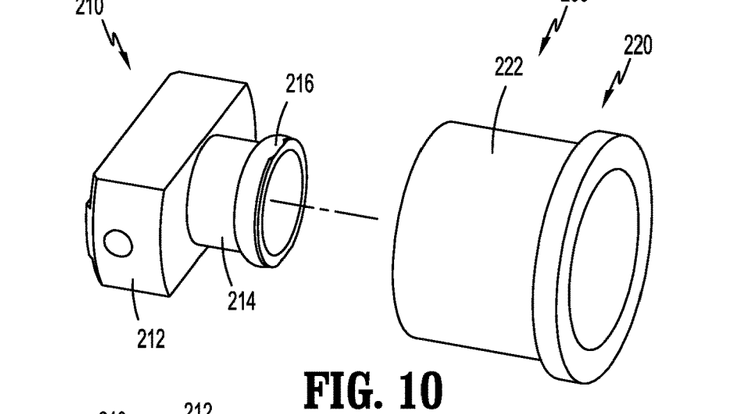
FIG. 10 is a perspective view of the tension gage housing and the tension gage anchor shown in FIG. 9, with parts separated.
Figure 11:
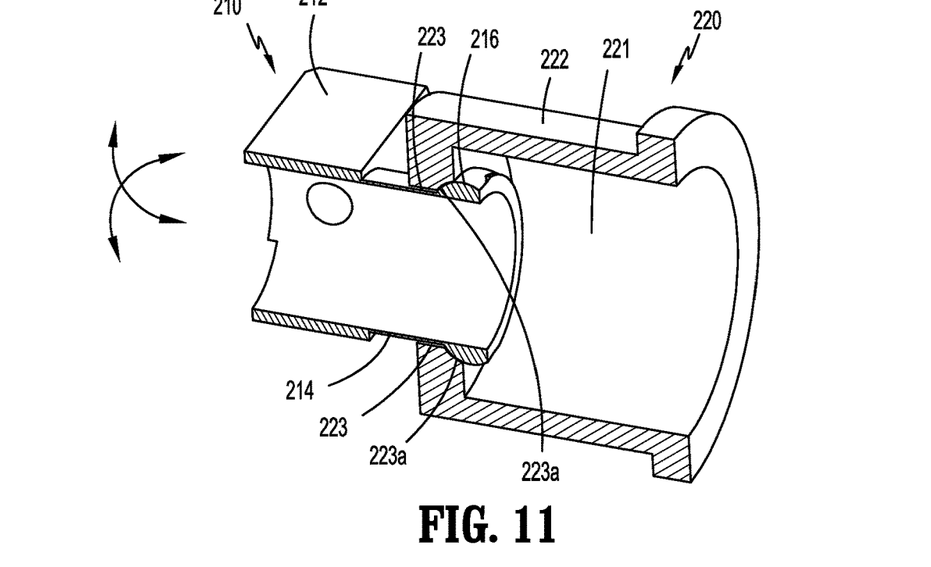
FIG. 11 is a cross-sectional side view taken along line 11-11 shown in FIG. 9.

FIGS. 9-11 illustrate another mechanism for measuring uniaxial strain in the adapter assembly 14 according to an aspect of the disclosure, shown generally as strain gage assembly 200. The strain gage assembly 200 is substantially similar to the strain gage assembly 100 described above, and therefore will only be described in detail as relates to the differences therebetween.

The strain gage assembly 200 includes a ball-in-socket configuration. More particularly, the strain gage assembly 200 includes a tension gage housing 210 having a rounded flange 216 supported on a free end of an extension portion 214 of the tension gage housing 210. A tension gage anchor 220 defines an opening 223 having a rounded proximal portion 123a. The rounded configuration of the rounded flange 216 and the rounded proximal portion 123a of the opening 223 permits off-axial movement of the tension gage housing 210 relative to the tension gage support 220, e.g., rotational degrees of freedom. This configuration allows the strain gage output to be unaffected by changes in the force vector direction and component location.

Persons skilled in the art will understand that the devices and methods specifically described herein and illustrated in the accompanying drawings are non-limiting exemplary aspects of the disclosure. It is envisioned that the elements and features illustrated or described in connection with one exemplary device may be combined with the elements and features of another without departing from the scope of the disclosure. As well, one skilled in the art will appreciate further features and advantages of the disclosure based on the above-described aspects. Accordingly, the disclosure is not to be limited by what has been particularly shown and described, except as indicated by the appended claims.

What is claimed is:

1. A strain gauge assembly for use in a circular stapling device, the assembly comprising:
    a housing including a base portion, an extension portion having a free end extending from the base portion and a flange disposed on the free end of the extension portion, the housing defining a longitudinal passage to receive a trocar assembly of the circular stapling device;
    a plurality of strain gauges disposed about the extension portion of the housing, the plurality of strain gauges being configured to measure an axial load on the trocar assembly received within the longitudinal passage of the housing;
    an anchor supporting the housing, the anchor including a cylindrical portion having an end and a rim disposed about the end of the cylindrical portion, the anchor defining a cylindrical recess and an opening in communication with the cylindrical recess, the cylindrical recess receiving the flange of the housing when the extension portion of the housing is received within the opening; and
    a support received about the housing and in engagement with the anchor, the support including a collar for supporting a reload assembly of the circular stapling device.

2. The strain gauge assembly of claim 1, wherein the plurality of strain gauges includes three strain gauges.

3. The strain gauge assembly of claim 1, wherein the housing defines first and second openings in communication with the longitudinal passage of the housing for receiving respective first and second retention pins.

4. The strain gauge assembly of claim 3, wherein the first and second retention pins are selectively engageable with a trocar housing of the trocar assembly.

5. The strain gauge assembly of claim 1, wherein the support includes a pair of extensions in operable engagement with the rim of the anchor.

6. The strain gauge assembly of claim 1, wherein the flange of the housing includes a rounded outer surface and the opening in the anchor includes a rounded portion corresponding to the rounded outer surface of the flange configured to permit movement of the housing relative to the anchor.

7. The strain gauge assembly of claim 1, wherein the anchor defines first inner and outer slots on a first side of the opening and second inner and outer slots on a second side of the opening, the first and second inner and outer slots being configured to receive inner and outer bands of a drive assembly.

8. The strain gauge assembly of claim 1, wherein the support is configured to transfer a load from the reload assembly to the housing.

9. An adapter assembly for connecting a reload assembly to a handle assembly, the adapter assembly comprising:
    a distal portion configured for operable engagement with the reload assembly;
    a proximal portion configured for operable engagement with a handle assembly;
    a strain gauge assembly disposed within the distal portion, the strain gauge assembly including a housing, an anchor secured to the housing, and a support disposed about the housing and in engagement with the anchor, the housing defining a longitudinal passage; and
    a trocar assembly received within the housing of the strain gauge assembly, the trocar assembly including a trocar housing and a trocar member slidably disposed within the trocar housing, wherein the strain gauge assembly is configured to measure the tensile load experienced by the trocar assembly during a surgical stapling procedure.

10. The adapter assembly of claim 9, wherein the housing includes a base portion, an extension portion having a free end extending from the base portion, and a flange disposed on the free end of the extension portion.

11. The adapter assembly of claim 10, where the strain gauge assembly includes a plurality of strain gauges disposed about the extension portion of the housing.

12. The adapter assembly of claim 11, wherein the plurality of strain gauges is configured to measure an axial load on the trocar assembly when the trocar assembly is received within the longitudinal passage of the housing.

13. The adapter assembly of claim 12, wherein the anchor includes a cylindrical portion having an end and a rim disposed about the end of the cylindrical portion, the anchor defining a cylindrical recess and an opening in communication with the cylindrical recess, the cylindrical recess receiving the flange of the housing when the extension portion of the housing is received within the opening.

14. The adapter assembly of claim 13, wherein the support includes a collar for supporting the reload assembly of the circular stapling device.

15. The adapter assembly of claim 13, wherein the support includes a pair of extensions in operable engagement with the rim of the anchor.

16. The adapter assembly of claim 11, wherein the plurality of strain gauges includes three strain gauges.

17. The adapter assembly of claim 11, wherein the flange of the housing includes a rounded outer surface and the opening in the anchor includes a rounded portion corresponding to the rounded outer surface of the flange configured to permit movement of the housing relative to the anchor.

18. The adapter assembly of claim 10, wherein the housing defines first and second openings in communication with the longitudinal passage of the housing for receiving respective first and second retention pins.

19. The adapter assembly of claim 18, wherein the trocar assembly includes a trocar housing, and the first and second retention pins are selectively engageable with the trocar housing of the trocar assembly.

20. The adapter assembly of claim 9, wherein the support is configured to transfer a load from the reload assembly to the housing.

* * * * *